US008076448B2

(12) United States Patent
Moore et al.

(10) Patent No.: US 8,076,448 B2
(45) Date of Patent: Dec. 13, 2011

(54) PREPARATION OF BIODEGRADABLE POLYESTERS WITH LOW-BURST PROPERTIES BY SUPERCRITICAL FLUID EXTRACTION

(75) Inventors: Lester Moore, Fort Collins, CO (US); Richard L. Norton, Ft. Collins, CO (US)

(73) Assignee: Tolmar Therapeutics, Inc., Fort Collins, CO (US)

( * ) Notice: Subject to any disclaimer, the term of this patent is extended or adjusted under 35 U.S.C. 154(b) by 147 days.

(21) Appl. No.: 12/421,535

(22) Filed: Apr. 9, 2009

(65) Prior Publication Data
US 2009/0305957 A1   Dec. 10, 2009

Related U.S. Application Data

(63) Continuation of application No. PCT/US2007/021749, filed on Oct. 11, 2007.

(60) Provisional application No. 60/850,744, filed on Oct. 11, 2006.

(51) Int. Cl.
C08F 6/00       (2006.01)
C08J 3/00       (2006.01)

(52) U.S. Cl. .......... 528/492; 514/7; 514/9; 514/259.41; 528/271; 528/272

(58) Field of Classification Search .......... 514/7, 9, 514/259.41; 528/271, 272
See application file for complete search history.

(56) References Cited

U.S. PATENT DOCUMENTS

| | | | |
|---|---|---|---|
| 4,728,721 A | 3/1988 | Yamamoto et al. | |
| 4,810,775 A | 3/1989 | Bendix et al. | |
| 4,938,763 A | 7/1990 | Dunn et al. | |
| 5,324,519 A | 6/1994 | Dunn et al. | |
| 5,478,921 A * | 12/1995 | Roby et al. .................... | 528/480 |
| 5,585,460 A | 12/1996 | Yamada et al. | |
| 5,702,716 A | 12/1997 | Dunn et al. | |
| 5,744,153 A | 4/1998 | Yewey et al. | |
| 5,981,694 A | 11/1999 | Gruber et al. | |
| 5,990,194 A | 11/1999 | Dunn et al. | |
| 6,143,314 A | 11/2000 | Chandrashekar et al. | |
| 6,261,583 B1 | 7/2001 | Dunn et al. | |
| 6,395,293 B2 | 5/2002 | Polson et al. | |
| 6,461,631 B1 | 10/2002 | Dunn et al. | |
| RE37,950 E | 12/2002 | Dunn et al. | |
| 6,528,080 B2 | 3/2003 | Dunn et al. | |
| 6,565,874 B1 | 5/2003 | Dunn et al. | |
| 6,630,155 B1 | 10/2003 | Chandrashekar et al. | |
| 6,773,714 B2 | 8/2004 | Dunn et al. | |
| 6,966,990 B2 | 11/2005 | Chattopadhyay et al. | |
| 7,019,106 B2 | 3/2006 | Yamamoto et al. | |
| 2006/0074010 A1* | 4/2006 | Chattopadhyay et al. ........ | 514/2 |

FOREIGN PATENT DOCUMENTS
WO   WO-2008045516 A1   4/2008

OTHER PUBLICATIONS

Formation of polymer particles with supercritical fluids: A review The Journal of Supercritical Fluids, vol. 34, Issue 3, Jul. 2005, pp. 287-308 Sang-Do Yeo, Erdogan Kiran.*
"European Application Serial No. 07839468.1, Communication mailed May 19, 2009", 2 pgs.
"European Application Serial No. 07839468.1, Response filed Jun. 19, 2009 to Communication mailed May 19, 2009", 4 pgs.
"European Application Serial No. 07839468.1, Supplementary European Search Report mailed Dec. 29, 2009", 5 pgs.
"International Application Serial No. PCT/US07/21749, International Search Report mailed Jan. 30, 2008", 3 pgs.
"International Application Serial No. PCT/US07/21749, Written Opinion mailed Jan. 30, 2008", 6 pgs.
Taylor, L. T., "Chapter 2—Properties of Supercritical Fluids", *Supercritical Fluid Extraction*, John Wiley & Sons, Inc., New Nork, NY, (1996), 7-27.
Vilegas, J. H. Y., et al., "Extraction of Low-Polarity Compounds (with Emphasis on Coumarin and Kaurenoic Acid) from Mikania glomerata ('Guaco') Leaves", *Phytochemical Analysis*, 8(5), (1997), 266-270.
"Canadian Application Serial No. 2,666,341, Voluntary Amendment filed Mar. 16, 2010", 5 pgs.
"Canadian Application Serial No. 2666341, Office Action mailed Sep. 7, 2010", 2 pgs.
"European Application Serial No. 07839468.1, Office Action mailed Jul. 28, 2010", 4 pgs.
"European Application Serial No. 07839468.1, Office Action Response Filed Dec. 7, 2010", 6 pgs.
"U.S. Appl. No. 12/421,535, filed Mar. 1, 2011 to Office Action mailed Sep. 7, 2010", 18 pgs.
Yeo, et al., "Formation of polymer particles with supercritical fluids", *A review. Journal of Supercritical Fluids*, vol. 34(3), (2005), 287-308.

* cited by examiner

*Primary Examiner* — Terressa Boykin
(74) *Attorney, Agent, or Firm* — Schwegman, Lundberg & Woessner P.A.

(57) ABSTRACT

The invention provides methods of extracting a biodegradable polyester with a supercritical fluid effective to obtain a purified biodegradable polyester, such as a purified biodegradable poly(lactide-glycolide) (PLG). The supercritical fluid can be carbon dioxide at an elevated pressure, or can be carbon dioxide with one or more cosolvents. Methods for carrying out stepwise purification of the biodegradable polyester at multiple pressures or multiple temperatures, or both, are also provided. When the polyester is PLG, a purified PLG copolymer is obtained having a narrowed molecular weight distribution with respect to the unpurified polyester. The purified PLG copolymer can have a polydispersity index of less than about 1.7, less than about 2% monomers, and less than about 10% oligomers. The purified PLG copolymer can exhibit a reduced initial burst effect when incorporated into a controlled release formulation such as a flowable implant adapted to be injected into body tissues.

28 Claims, 3 Drawing Sheets

- ■ GROUP I, STANDARD PLG LOT 2137
- ◆ GROUP II, SOLVENT PRECIPITATED PLG LOT 2137
- △ GROUP III, SOLVENT PRECIPITATED PLG LOT 1826-58
- ○ GROUP IV, SOLVENT PRECIPITATED PLG LOT 2190-28A
- ▲ GROUP V, FRACTION 5 SCF PURIFIED PLG LOT 2137
- ● GROUP VI, FRACTION 6 SCF PURIFIED PLG LOT 2137

PREPARATION OF BIODEGRADABLE POLYESTERS WITH LOW-BURST PROPERTIES BY SUPERCRITICAL FLUID EXTRACTION

Cross-Reference to Related Applications

This application is a continuation under 35 U.S.C. §111(a) of International Application No. PCT/US2007/021749 filed Oct. 11, 2007 and published in English as WO 2008/045516A1 on Apr. 17, 2008, which claims priority under 35 U.S.C. §119(e) to U.S. Application Ser. No. 60/850,744, filed Oct. 11, 2006, both of which applications are incorporated herein by reference in their entireties.

BACKGROUND

Methods such as solvent extraction and precipitation are currently employed to purify various types of polymers, such as those biodegradable polyesters used in controlled release formulations for implantation within body tissue. Dissolution of a sample of a polyester in a solvent and precipitation of certain fractions with a miscible non-solvent has been used to prepare materials with advantageous properties. For example, it has been found that certain methods of purification including selective solvent precipitation can provide biodegradable polyesters wherein the "initial burst effect", an excessively high initial rate of release of a medicinal compound incorporated into the polyester upon implantation into body tissues, is reduced relative to that observed using the unpurified polyester.

For example, U.S. Pat. No. 4,728,721 discusses the presence of water-soluble unreacted monomers and water-soluble low molecular weight oligomers within the copolymers that are used to form microcapsules into which bioactive agents are incorporated. According to the inventors therein, the presence of these impurities tends to increase the initial burst effect. The patent provides methods for removal of some of these impurities by washing of a solid form of the polyester with water, or by dissolving the polyester in a water-soluble organic solvent and adding the solution to water.

U.S. Pat. No. 5,585,460 discusses the processing of polyesters used for the preparation of microcapsules, wherein polyesters are dissolved in a water-soluble organic solvent and precipitated in water to provide polyesters that are stated to have components with molecular weights under 1,000 (1 kDa) of less than about 3%.

U.S. Pat. No. 4,810,775 describes a process for purifying partly crystalline or amorphous polyesters wherein high shear forces are applied at the time of contacting the polyester with a precipitating agent such as water so that minute particles of the polyester are obtained. This patent describes that such treatment results in the removal of residual monomers and catalysts from the polyester.

U.S. Pat. No. 7,019,106 discusses a process for producing a lactic acid polyester of 15,000 to 50,000 in weight-average molecular weight, the content of polyesteric materials having not more than about 5,000 in weight-average molecular weight therein being not more than about 5% by weight. The process is characterized by hydrolysis of a high molecular weight lactic acid polyester and precipitation of the hydrolyzed product, which is stated to provide for a reduced burst effect.

U.S. patent application Ser. No. 60/901,435, filed Feb. 15, 2007 by the inventors herein, discusses a solvent precipitation process for producing a poly(lactide glycolide) polyester fraction ("PLGp") that is advantageous in terms of reducing the initial burst effect.

A drawback of solvent extraction or precipitation processes is that they typically require relatively large amounts of organic solvents that are hazardous, difficult to handle, or difficult to dispose of. The typical organic solvents, which include methylene chloride and chloroform, are hazardous to humans (i.e., they are toxic or carcinogenic) and are hazardous to the environment. Considering the industrial scale on which the extraction processes would need to be performed in order to provide industrial quantities (e.g., kilograms or tons) of polymers, large quantities of organic solvents would be required. The high cost of disposing the organic solvents is an additional disadvantage of the current extraction procedures.

Supercritical fluid extraction refers to an extraction wherein a fluid at a temperature and pressure above its critical point is employed; or a fluid above its critical temperature, regardless of pressure, is employed. Below the critical point, the fluid can coexist in both gas and liquid phases, but above the critical point there is only one phase. Equipment, techniques, procedures, solvents and conditions (e.g., time, temperature and pressure) for carrying out supercritical fluid extraction are known to those skilled in the art. See, e.g., Supercritical Fluid Science and Technology, ACS Symposium Series: 406, K. P. Johnston, et al., editor, American Chemical Society, (1989), pp. 1-550; Supercritical Fluid Extraction-Principals and Practice, Second Edition, M. A. McHugh, et al., editors, Butterworth-Heinemann, (1994), pp. 1-512; Johnston, K. P. et al., "Supercritical Fluid Science and Technology", ACS Symposium Series 406, American Chemical Society, (1989), 1-550; McHugh, Mark J., Supercritical Fluid Science and Technology, ACS Symposium Series: 406, K. P. Johnston, et al., editor, American Chemical Society, (1989), pp. 1-550; McHugh, M., et al., Supercritical Fluid Extraction-Principles and Practice, Second Edition, M. A. McHugh, et al., editors, Butterworth-Heinemann, (1994), pp. 1-512; McHugh, M., et al., Supercritical Fluid Extraction, 2nd Edition, (1994); Taylor, L. T., "Properties of Supercritical Fluids", Supercritical Fluid Extraction. Chapter 2, John Wiley & Sons, New York, (1996), pp. 7-27; and Vilegas, J. H., et al., "Extraction of Low-polarity Compounds with Emphasis on Coumarin and Kaurenoic Acid from Mikania glomerata (Guaco) Leaves", Phytochem. Anal., 8, Abstract Obtained from CAPLUS, Document No. 127:316461, (1997), pp. 266-270.

Suitable solvents useful in supercritical fluid extraction are disclosed, e.g., Supercritical Fluid Science and Technology, ACS Symposium Series: 406, K. P. Johnston, et al., editor, American Chemical Society, (1989), pp. 1-550; Supercritical Fluid Extraction-Principals and Practice, Second Edition, M. A. McHugh, et al., editors, Butterworth-Heinemann, (1994), pp. 1-512; Johnston, K. P. et al., "Supercritical Fluid Science and Technology", ACS Symposium Series 406, American Chemical Society, (1989), 1-550; McHugh, Mark J., Supercritical Fluid Science and Technology, ACS Symposium Series: 406, K. P. Johnston, et al., editor, American Chemical Society, (1989), pp. 1-550; McHugh, M., et al., Supercritical Fluid Extraction-Principles and Practice, Second Edition, M. A. McHugh, et al., editors, Butterworth-Heinemann, (1994), pp. 1-512; McHugh, M., et al., Supercritical Fluid Extraction, 2nd Edition, (1994); Taylor, L. T., "Properties of Supercritical Fluids", Supercritical Fluid Extraction. Chapter 2, John Wiley & Sons, New York, (1996), pp. 7-27; and Vilegas, J. H., et al., "Extraction of Low-polarity Compounds with Emphasis on Coumarin and Kaurenoic Acid from Mikania glomerata (Guaco) Leaves", Phytochem. Anal., 8, Abstract Obtained from CAPLUS, Document No. 127:316461, (1997), pp. 266-270. One such supercritical fluid, not available for use as a solvent under conditions of standard temperature and pressure, is carbon dioxide. Carbon dioxide is a naturally occurring component of the atmosphere, produced by living organisms, and while there may be concern about excessive levels in the atmosphere in relation to global warming, in no way is carbon dioxide generally considered to be toxic or environmentally damaging in the way that, for example, chloroform is. Therefore, there is a need for industrial processes that can substitute the relatively non-toxic carbon dioxide as an extraction solvent for the more toxic halocarbons and the like in purification processes for polymer such as biodegradable polyesters that provide a product with desirable properties.

SUMMARY OF THE INVENTION

An embodiment according to the present invention is directed to a method for preparing a purified biodegradable polyester, for example a purified poly(lactide-glycolide) referred to hereinafter as a PLG copolymer, by extraction of the polyester with a supercritical fluid comprising carbon dioxide. The purified biodegradable polyester so obtained can have a narrower molecular weight distribution than the starting sample. When incorporated into a controlled release formulation for a bioactive substance, the purified copolymer can provide for a reduced initial burst effect of the bioactive substance.

An embodiment of the invention provides a method for obtaining a purified biodegradable polyester, the method comprising extracting a biodegradable polyester with a supercritical fluid comprising carbon dioxide to obtain the purified biodegradable polyester.

An embodiment of the invention provides a method wherein the biodegradable polyester is poly(DL-lactide-glycolide) (PLG) and the purified biodegradable polyester is a purified PLG copolymer. The biodegradable polyester can also be a PLG previously purified by a solvent precipitation process, such as a PLGp.

In an embodiment of the invention, extraction can be carried out repeatedly at different temperatures or pressures to fractionate the biodegradable polyester such as PLG.

An embodiment of the invention provides a method for obtaining purified poly(DL-lactide-glycolide) (PLG) by extracting a poly(DL-lactide-glycolide) material having an average molecular weight (Mw) of about 15 kDa to about 45 kDa with a supercritical fluid comprising carbon dioxide at a temperature above about 40° C. and a pressure above about 1,000 psi, to obtain a purified PLG copolymer wherein the purified PLG copolymer has a narrower molecular weight distribution (polydispersity index) than the PLG. The polydispersity index of the purified PLG copolymer can be less than about 1.7.

Another embodiment provides a purified polyester obtained by the method of the invention, or, more specifically, a purified PLG copolymer according to the method of the invention. The SFE-purified PLG copolymer can have a narrower distribution of individual polymer chain molecular weights, a reduced oligomer content, and a reduced monomer content.

Another embodiment of the invention provides a controlled release formulation comprising a flowable composition comprising the SFE-purified biodegradable PLG copolymer or polyester, an organic solvent having at least some solubility in body fluids, and a bioactive substance. The bioactive substance can be, for example, octreotide, GHRP-1, or risperidone.

BRIEF DESCRIPTION OF THE DRAWINGS

Embodiments of the invention may be best understood by referring to the following description and accompanying drawings which illustrate such embodiments. The numbering scheme for the Figures included herein are such that the leading number for a given reference number in a Figure is associated with the number of the Figure. In the drawings.

DETAILED DESCRIPTION OF THE INVENTION

Figure 1:
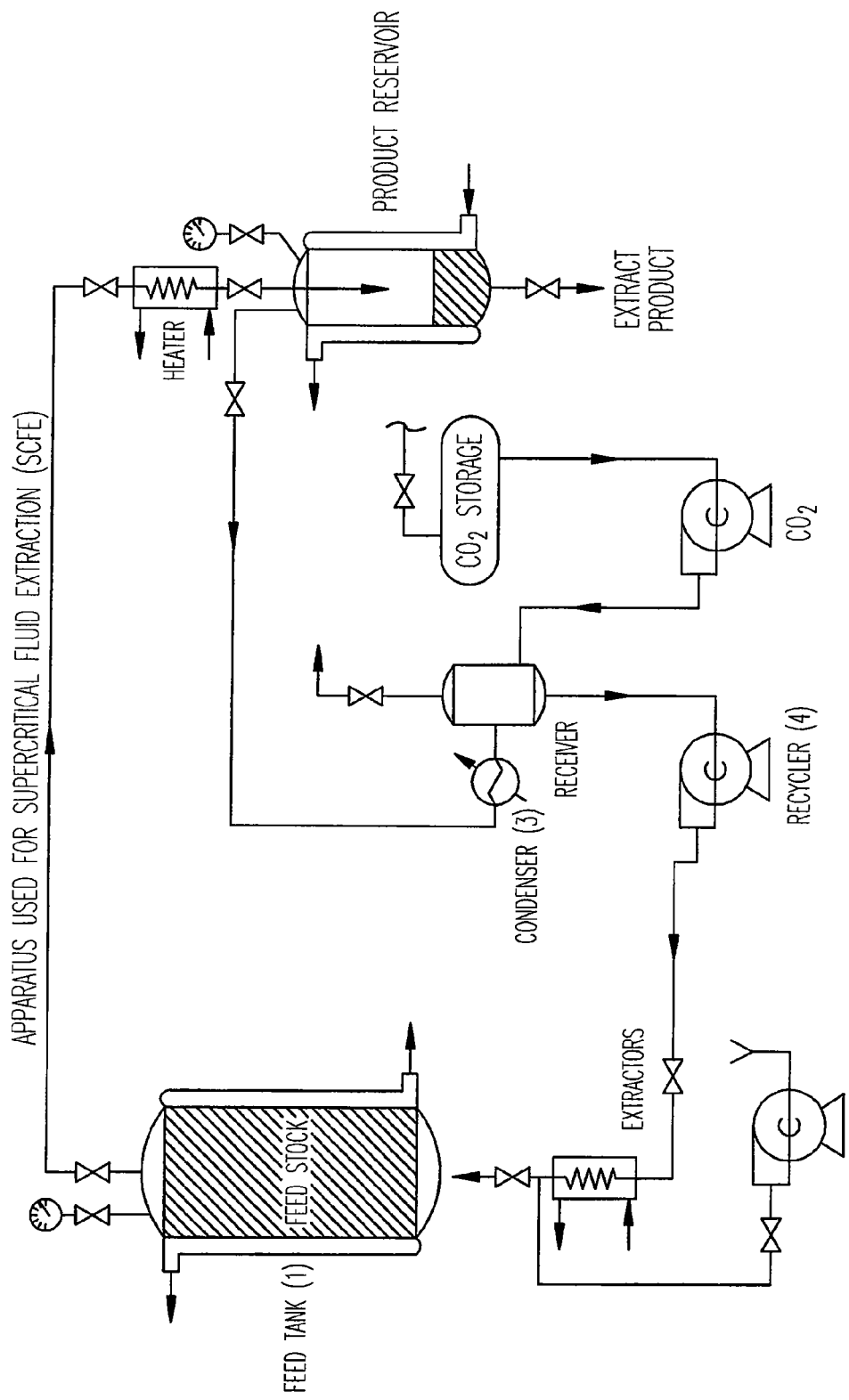
FIG. 1 is a schematic diagram an apparatus suitable for supercritical fluid extraction according to the method of the invention.

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present invention relates to methods of purifying polyesters. When describing the methods of purifying polyesters, the following terms have the following meanings, unless otherwise indicated.

Definitions

Unless stated otherwise, the following terms and phrases as used herein are intended to have the following meanings:

"Supercritical fluid extraction" refers to an extraction wherein a fluid at a temperature and pressure above its "critical point" is employed; or a fluid above its critical temperature, regardless of pressure, is employed. The "critical point" of a fluid is the point defined by temperature or a combination of temperature and pressure, wherein below the critical point, the fluid can coexist in both gas and liquid phases, but above the critical point there is only one phase. In a supercritical fluid extraction, thermodynamic and transport properties of supercritical fluid are a function of density, which depends strongly on the fluid's pressure and temperature. The density may be adjusted from a gas-like value of 0.1 g/ml to a liquid-like value as high as 1.2 g/ml. Furthermore, as conditions approach the critical point, the effect of temperature and pressure on density becomes much more significant. For example, increasing the density of the supercritical solvent (e.g., carbon dioxide) from 0.2 to 0.5 g/ml requires raising the pressure from 85 atm to 140 atm (8.6 megapascals to 14.2 megapascals) at 158° F. (70° C.), but at 95° F. (35° C.) the required change is only from 65 atm to 80 atm (6.61 Mpa to 8.1 Mpa).

As used herein, supercritical fluid extraction includes fractional supercritical fluid extraction. As used herein, "fractional supercritical fluid extraction" (hereinafter "FSFE") refers to a multi-step procedure wherein the supercritical fluid extraction is carried out at one temperature and pressure for a given period of time and is then carried out at one or more other temperatures and/or one or more pressures. These temperatures and/or pressures can be increased incrementally for a sequential series of extractions. By "sequential" is meant that the polyester is extracted under one set of conditions, the solution of the solute fraction in the supercritical fluid is removed, e.g. by filtration or centrifugation, then the residual polyester is extracted under a second, third, etc. set of conditions, repeating the operation. When increasing temperatures and/or pressures are employed in sequential extractions, typically different polyester fractions are recovered from the various sequential extracts, which can be kept separate from each other for this purpose.

As used herein, a "co-solvent" refers to any solvent (e.g., aqueous solution, organic solvent or gas), in addition to carbon dioxide, that can be employed in a supercritical fluid extraction (SFE). Examples of co-solvents include hydrocarbon, alcohols, inert gasses, and other relatively volatile compounds as is discussed in greater detail below.

A "controlled release formulation" as the term is used herein refers to a formulation adapted to release a contained bioactive substance into body tissues over a period of time. An example of a controlled release formulation within the meaning herein is "liquid delivery system" or a "flowable delivery system," a combination of biodegradable polyester, a bioactive agent and an organic solvent, such as in the Atrigel® system. The organic solvent has at least some solubility in water and in body fluids. An example is N-methylpyrrolidone (NMP). Upon injection of the flowable material into tissue, the solvent disperses into the tissue and body fluid diffuses into the injected bolus, thereby causing coagulation of the polyester into a solid or semi-solid mass. Solvents that can be used with the inventive polyesters for a liquid or flowable delivery system include N-methylpyrrolidone, N,N-dimethylformamide, N,N-dimethylacetamide, dimethylsulfoxide, triacetin, polyethylene glycol 200, polyethylene glycol 300, or methoxypolyethylene glycol 350, all of which have at least some solubility in water and in body fluids. See, for example, U.S. Pat. Nos. 6,773,714; 6,630,155; 6,565,874; 6,528,080; RE37,950; 6,461,631; 6,395,293; 6,261,583; 6,143,314; 5,990,194; 5,744,153; 5,702,716; 5,324,519; 4,938,763 and references cited therein, which are incorporated by reference herein.

Often, an initial dispersion of the solvent out of the mass will carry the bioactive agent with it into surrounding tissues, thereby producing a burst effect. A solid implant, of the monolithic or of the microparticulate type, also displays a burst effect due to the presence of bioactive agent on and near the surface of the implant, and due to the presence of easily leached bioactive agent within the micro-channels and mesopores that form within the implant as a result of its initial interaction with body fluid.

The terms "polyester" or "copolymer" as used herein refer to substantially linear polyesters, also referred to herein as "PLG copolymers," predominantly formed of monomeric lactate and glycolate hydroxyacids, or lactide and glycolide dimeric hydroxyacids, and include compositions referred to in the art as poly(lactate-glycolate), poly(lactate(co)glycolate), poly(lactide-glycolide), poly(lactide(co)glycolide), PLG, PLGH, and the like, with the understanding that additional moieties may be included, such as core/initiator groups (for example, diols, triols, polyols, hydroxyacids, and the like), capping groups (for example, esters of terminal carboxyl groups, and the like) and other pendant groups or chain extension groups covalently linked to or within a polyester backbone, including groups that cross-link the substantially linear polyester molecular chains, without departing from the meaning assigned herein. PLG copolymers, as the term is used herein, includes molecular chains with terminal hydroxyl groups, terminal carboxyl groups (i.e., acid-terminated, sometimes termed PLGH) and terminal ester groups (i.e., capped).

As used herein, the term "polyester material" or "copolymer material" refers to the physical assembly or the combined mass of a plurality of individual polyester or PLG copolymer molecules (molecular chains) in a given sample, respectively, each of which molecules (molecular chains) has its own defined molecular weight in the usual chemical sense of the word. A "polyester material" or "PLG copolymer material" as used herein usually is composed of a set of individual polyester or PLG copolymer molecules having various different individual molecular weights. Thus, when the molecular weight of such a polyester material or a copolymer material is referred to, it is an average molecular weight. Without further characterization, such an average molecular weight is a weight average molecular weight as used herein. The full description, weight average molecular weight, may be used synonymously. If the average molecular weight being referred to is the number-average molecular weight, it will be explicitly stated in this specification. When the individual molecular weights of the component individual molecules (molecular chains) is referred to, the term "individual molecular weight" is used in this specification. Weight average molecular weights are determined by the use of gel permeation chromatography (GPC) with reference to polystyrene standards, as is well known in the art.

The term "polydispersity index" as used herein is defined as the weight-average molecular weight of a sample of a polyester material divided by the number-average molecular weight of the sample of the polyester material. The definitions of the terms "weight-average molecular weight" and "number-average molecular weight" are well-known to those of skill in the art. The polydispersity index is well-known to characterize the distribution of molecular weights in a polyester. The higher the value of the polydispersity index, the broader the spread of individual molecular weights of the polyester molecular chains making up the polyester material. The lower the value of the polydispersity index, the more uniform and tightly grouped are the individual molecular weights of the individual polyester molecules making up the polyester material in question. In the unlikely event that every polyester molecule in the polyester material were identical, the weight-average molecular weight and the number-average molecular weight would be identical, and thus the polydispersity index ("PDI") would be unity.

The terms "lactate" and "glycolate" as used herein, depending upon context, refer to either the hydroxyacids, lactic acid and glycolic acid respectively, or their salts (lactates and glycolates) which are used as reagents in preparation of inventive copolymers, or refer to those moieties as residues incorporated via ester bonds into the inventive polyester molecular chains. When a copolymer is formed by polymerization of lactic acid (lactate) and glycolic acid (glycolate), each molecular chain consists of individual lactate and glycolate monomeric units incorporated into the copolymer molecular chain. The terms "lactide" and "glycolide" as used herein, depending upon context, refer to either the cyclic dimeric esters of lactate and glycolate respectively when referring to reagents used in preparation of inventive copolymers, or refer to those segments as incorporated ring-opened dimers in the formed polyester molecular chains. Thus, a statement about polymerization of lactide and glycolide refers to a polymerization reaction of the cyclic dimeric esters, whereas a statement about a lactide or glycolide residue within a copolymer molecular chain refers to that grouping of atoms, ring-opened, and incorporated into the copolymer chain. When a copolymer is formed by polymerization of lactide and glycolide, each incorporated lactide or glycolide residue is believed to consist of a pair of lactate or glycolate monomeric units, respectively. It is understood that when a lactide and glycolide residue in a copolymer molecular chain is referred to, the terms mean double (dimeric) units of two lactate (L-L), or two glycolate (G-G), residues in the molecular chain, respectively, such as is believed to result from the polymerization of lactide and glycolide. When a lactate (L) or a glycolate (G) residue in a copolymer molecular chain is referred to, the terms mean single lactate (L) or glycolate (G) residues in the molecular chain, respectively, which can be within a lactide (L-L) or a glycolide (G-G) residue if the given lactate or glycolate is adjacent to another lactate or glycolate residue, respectively, regardless of the method used to prepare the copolymer molecular chain. As is most polymeric systems, this arrangement of residues is not all or none. Instead, the arrangement is a predominance. Thus, for the lactide and glycolide copolymers, a predominance of L-L and G-G residues will be present with some L and G (single) residues also present. The chemical reason underlying this characterization is the polymerization process. During polymerization, growing polyester chains are broken and reformed. This scission may split dimer residues and recombine single residues. For the lactate and glycolate copolymers, a predominance of L and G (single) residues will be present. This kind of polyester will have a relatively few sequences including repeats of dimer residues because of entropy factors.

It is understood that when the terms "lactic acid," "lactate," or "lactide" are used herein, that any and all chiral forms of the compounds are included within the terms. Thus, "lactic acid" includes D-lactic acid, L-lactic acid, DL-lactic acid, or any combination thereof; "lactide" includes DD-lactide, DL-lactide, LD-lactide, LL-lactide, or any combination thereof.

"Lactide," as the term is used herein when referring to a monomeric reagent, is a cyclic dimer of lactic acid as shown:

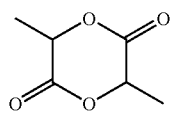

"Glycolide," as the term is used herein when referring to a monomeric reagent, is a cyclic dimer of glycolic acid as shown:

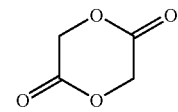

When referring to polyesters as "poly(lactide-glycolide)" or "PLG copolymers" a copolymer comprising both linear lactide and linear glycolide units incorporated into a linear polyester chain via ring opening reactions contains domains including the following two structures:

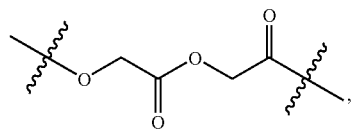

a polyglycolide segment, and

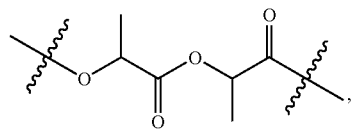

a polylactide segment. These segments can be randomly distributed along the length of the PLG copolymer chain. It is also understood that the PLG copolymer can be prepared by polymerization of lactic acid and glycolic acid, in which case individual lactate and glycolate units can be randomly distributed along the chain. However, a PLG copolymer prepared by ring-opening copolymerization of cyclic dimers lactide and glycolide is preferred in carrying out the inventive method.

A PLG copolymer according to the use herein has a weight average molecular weight, as is well known in the art, of about 5 kDa to about 55 kDa. Polyester chains of less than about 5 kDa molecular weight are referred to herein as "oligomers." The term "monomers" encompasses both lactic acid and glycolic acid, and lactide and glycolide, the cyclic dimers as shown above.

In the present application, the terms "burst effect" or "initial burst effect" are used to refer to the burst effects in which a higher than optimal rate of diffusion of a bioactive agent out of a controlled release formulation occurs during the solidification of a liquid delivery system and/or during the initial period following implantation of a preformed solid implant such as a monolithic or a microparticulate implant. The copolymers according to the present invention are particularly suitable for controlling this initial burst.

The term "low-burst" as used herein, such as a "low-burst copolymer material," refers to a phenomenon wherein this burst effect is minimized or reduced relative to that observed from a comparable art copolymer composition, while maintaining a desirable long-term release profile. When the phrases "reduced initial burst effect" or "the initial burst of the bioactive substance upon implantation within body tissues is reduced" are used, they refer to the initial burst effect of a controlled release formulation comprising a flowable composition comprising a SFE-purified polyester or a SFE-purified PLG copolymer after implantation in body tissues as being reduced with respect to the comparable formulation using an unpurified polyester or PLG copolymer.

By the term "biodegradable" is meant herein the property that an inventive polyester, when implanted in body tissue, exposed to body fluids of a living organism, or acted on by enzymes normally present in the living body of a mammal, undergoes hydrolysis and depolymerization such that a mass of the polyester eventually, over time, erodes, dissolves, dissipates and dematerializes. Preferably the degradation products are non-toxic and water-soluble.

Methods of Purifying Polyesters Employing SFE

Referring to FIG. 1, an apparatus suitable for practicing the inventive methods of purifying a biodegradable polyester by means of supercritical fluid extraction (SFE) is shown. The starting polyester, such as PLG, can be introduced into a feed tank, also referred to as an extraction vessel, (1) through the opened lid on the top. The polyester is heated at an elevated pressure in a solvent under supercritical conditions (e.g., carbon dioxide, or a solvent that includes carbon dioxide). The solution of the dissolved polyester fraction in the fluid is transferred to a product reservoir (2). The fluid is removed, such as be evaporation, from the solution, leaving the extracted polyester fraction, which can be recovered. The evaporated fluid is passed though a condenser (3) and subsequently recycled into the extraction vessel (1) through a recycler (4). The solid undissolved polyester left in the extraction vessel can then optionally be extracted again, for example with a supercritical fluid under higher pressure, held at a higher temperature, or both, in a sequential set of extractions. Again, the polyester fraction dissolving can be transferred in solution into the product reservoir, when the fluid can be removed by evaporation as before, providing a polyester that can have different properties, such as weight-average molecular weight (Mw), and polydispersity index, than the first polyester fraction obtained in the lower temperature/ pressure extraction. This process can be repeated iteratively, providing a series of fractions of the biodegradable polyester, for example, PLG copolymer. Each fraction can have unique properties, due to the differing weight-average molecular weights, polydispersity indices, and molecular compositions of each fraction obtained in multiple sequential extractions.

Any biodegradable polyester can be purified as described herein. Examples of suitable biodegradable polyester polyesters are found, e.g., in U.S. Pat. Nos. 6,773,714; 6,630,155; 6,565,874; 6,528,080; RE37,950; U.S. Pat. Nos. 6,461,631; 6,395,293; 6,261,583; 6,143,314; 5,990,194; 5,744,153; 5,702,716; 5,324,519; 4,938,763 and references cited therein.

A biodegradable polyester that can be purified as described herein can be a PLG that has been purified by a step of solvent precipitation prior to carrying out the supercritical fluid extraction of the invention. For example, a PLG that has been purified by dissolving in a solvent and precipitation with a non-solvent, such as is described in U.S. patent application Ser. No. 60/901,435, filed Feb. 15, 2007 by the inventors herein, referred to hereinafter as a "PLG(p)" or a "PLGp," can be further purified by the inventive method herein. The purification can include removal of solvent and/or non-solvent residues.

A polyester can be purified according to the method of the invention employing supercritical fluid extraction. Supercritical fluid extraction employs a fluid in a supercritical state, as is defined for the particular fluid composition in terms of pressure and temperature. Every fluid material has a characteristic combination of pressure and temperature termed a "critical point," as defined above, and once those parameters are exceeded, the fluid exists in the supercritical state. The fluid or solvent employed in supercritical fluid extraction may be a single compound or may be a mixture of compounds. Suitable exemplary co-solvents include Xenon (Xe), Freon-23, ethane, $N_2O$, $SF_6$, propane, ammonia, ethylene, n-$C_4H_{10}$, methylene chloride, chloroform, $C_6H_5CF_3$, p-Cl-$C_6H_4CF_3$, lower alcohols (e.g., methanol, ethanol, 1-propanol, 2-propanol, and 1-hexanol), 2-methoxyethanol, ethers (e.g., diethyl ether, tetrahydrofuran and 1,4-dioxane), substituted hydrocarbons (e.g., acetonitrile), propylene carbonate, N,N-dimethylacetamide, dimethyl sulfoxide, N-methylpyrrolidone, carboxylic acids (e.g., formic acid), water, carbon disulfide, lower ketones (e.g., acetone), unsubstituted hydrocarbons (e.g., hexanes and pentanes), unsubstituted aromatics (benzene), and substituted aromatics (e.g., toluene). The co-solvent can be present in any suitable amount. Typically, the co-solvent can be present in at least about 1 wt. %, in about 1 wt. % to about 50 wt. %, in about 1 wt. % to about 30 wt. %, or in about 1 wt. % to about 10 wt. % of the solvent system.

The physical properties of carbon dioxide make it particularly attractive as a solvent for supercritical fluid extraction. Carbon dioxide is a major component of the atmosphere and is therefore relatively safe and abundant. In addition, carbon dioxide is relatively inexpensive. Compared to most other suitable solvents, carbon dioxide is environmentally friendly as it will not harm the atmosphere at the quantities used in the methods of the invention. Moreover, carbon dioxide is non-flammable and non-explosive. Further, carbon dioxide leaves no substantial residue or remnant upon evaporation.

Carbon dioxide also possesses physical properties which enable it to change polarity over the temperature range and pressure range normally employed in supercritical fluid extraction. As a result, carbon dioxide may act as a non-polar solvent at one temperature and pressure but may act as a polar solvent at another temperature and pressure. By varying the temperature and pressure, the solvent properties may be modified. This allows for the isolation of more than one compound using a single solvent system, for example using multiple sequential extractions at increasing temperatures and/or pressures.

The co-solvent can be employed for several practical reasons. The co-solvent can modify the physical properties of the solvent. For example, a co-solvent may be useful to modify the polarity, critical temperature, critical pressure, etc., of the solvent. The co-solvent can decrease the time necessary for extraction, which decreases the costs incurred for the extraction process and increases the efficiency of the extraction process. In addition, the use of at least one co-solvent can decrease the likelihood that the desired polyester will crystallize or gum out upon evaporation of the highly volatile solvent such as carbon dioxide. When the supercritical fluid extraction apparatus is dismantled and the desired polyester is obtained, the solvent (e.g., carbon dioxide) will typically evaporate very quickly, leaving the desired polyester as a solid or gum-like tar. As such, the use of the co-solvent allows the desired polyester to remain soluble in a solvent system for subsequent recovery or manipulation.

In an embodiment of the invention, the purified biodegradable polyester is a solid residue that remains following an extraction with a supercritical fluid. The supercritical fluid extraction can remove fractions of the starting unpurified polyester that tend to be detrimental to low initial burst, i.e., that cause high initial burst. The polyester that does not dissolve in the supercritical fluid can have lower contents of these undesirable constituents and consequently a narrower molecular weight distribution.

In another embodiment of the invention, the purified biodegradable polyester dissolves in the supercritical fluid, and is recovered therefrom. For example, in a series of multiple sequential extractions, certain fractions obtained in the sequence can have desirable properties in terms of low burst, having, for example, a narrowed molecular weight distribution. More specifically, fractions obtained after one or more early extractions, later in the sequence of multiple extractions, can have excellent properties in terms of low initial burst when incorporated into controlled release formulations such as flowable delivery systems like Atrigel®. These fractions obtained later in the sequence of multiple extractions also, by virtue of their dissolving in the supercritical fluid, can have low contents of excessively high molecular weight components, such as polymer molecules having individual molecular weights in excess of about 55 kDa, which remain as an insoluble residue and are thus absent in the fractions containing polyester molecules with the desired molecular weight properties.

In this way, the desired purified biodegradable polyesters can be obtained either from materials dissolving in the supercritical fluid extraction medium under certain defined conditions ("fractions"), or can be obtained from materials not dissolving in the supercritical fluid extraction medium ("residues") under other certain defined conditions.

Pressure

For the methods of purifying polyesters described herein, the supercritical fluid extraction can conveniently be carried out at a pressure of about 750 psi to about 12,000 psi. It is appreciated that those skilled in the art understand that higher pressures may enable faster or more complete extraction. Additionally, higher pressures may enable an extraction of polyester having a definite and relatively narrow molecular weight range. Specifically, the supercritical fluid extraction can conveniently be carried out at a pressure of about 1,000 psi to about 10,000 psi. More specifically, supercritical fluid extraction can conveniently be carried out at a pressure of about 4,000 psi to about 9,000 psi.

When the supercritical fluid extraction (SFE) is a fractional supercritical fluid extraction (FSFE), as effected by multiple sequential extractions, each of the individual supercritical fluid extractions can independently be carried out at pressures of about 750 psi to about 12,000; about 1,000 psi to about 10,000 psi; or about 4,000 psi to about 9,000 psi. Carrying out the fractional supercritical fluid extraction (FSFE) at multiple pressures may allow for the isolation or purification of one or more polyesters, each independently having a definite and relatively narrow molecular weight range. Each extraction in the sequence of sequential extractions can be performed with a successive sample of the supercritical fluid, that is, a fresh sample of the supercritical fluid. Alternatively, sequential extractions can be carried out using samples of the supercritical fluid of different compositions. For example, a series of sequential extractions can be carried out with supercritical carbon dioxide, wherein each successive extraction contains a regularly increasing content of a cosolvent.

Temperature

For the methods of purifying polyesters described herein, the supercritical fluid extraction can conveniently be carried out at any suitable temperature. It is appreciated that those skilled in the art understand that higher temperatures may enable faster or more complete extraction. Additionally, higher temperatures may enable an extraction of polyester having a definite and relatively narrow molecular weight range. For example, the supercritical fluid extraction can be carried out at a temperature of at least about 25° C. Specifically, the supercritical fluid extraction can conveniently be carried out at a temperature of about 40° C. to about 200° C. More specifically, supercritical fluid extraction can conveniently be carried out at a temperature of about 50° C. to about 100° C.

Each extraction in the sequence of sequential extractions can be performed with a successive sample of the supercritical fluid, that is, a fresh sample of the supercritical fluid. Alternatively, sequential extractions can be carried out using samples of the supercritical fluid of different compositions. For example, a series of sequential extractions can be carried out with supercritical carbon dioxide, wherein each successive extraction contains a regularly increasing content of a cosolvent.

When the supercritical fluid extraction (SFE) is a fractional supercritical fluid extraction (FSFE), each of the sequential individual supercritical fluid extractions can independently be carried out at any suitable temperature. For example, each of the individual supercritical fluid extractions can independently be carried out at a temperature of at least about 25° C.; about 40° C. to about 200° C.; or about 50° C. to about 100° C. Carrying out the fractional supercritical fluid extraction (FSFE) at multiple temperatures may allow for the isolation or purification of one or more polyesters, each independently having a definite and relatively narrow molecular weight range.

Controlled Release Formulation

A polyester, such as a PLG copolymer, purified by the present SFE method, can be used in the preparation of a controlled release formulation such as a flowable composition of the Atrigel® type, comprising the PLG copolymer, an organic solvent that has at least some solubility in water or body fluids, and a bioactive substance. Examples of such compositions and the polymers that have been used therein are described in, e.g., in U.S. Pat. Nos. 6,773,714; 6,630,155; 6,565,874; 6,528,080; RE37,950; U.S. Pat. Nos. 6,461,631; 6,395,293; 6,261,583; 6,143,314; 5,990,194; 5,744,153; 5,702,716; 5,324,519; 4,938,763 and references cited therein.

Use of a PLG copolymer purified by the method of the invention can serve to provide a controlled release formulation, such as of the Atrigel® type, that exhibits a reduced initial burst effect wherein an undesirably high amount of the bioactive substance is released into the body tissues in about the first 24 hours after implantation, relative to a controlled release formulation that uses a PLG copolymer that has not undergone such purification.

An organic solvent that has at least some solubility in water or body fluids can be, for instance, N-methylpyrrolidone (NMP), N,N-dimethylformamide (DMF), N,N-dimethylacetamide (DMA), or dimethylsulfoxide (DMSO).

A bioactive substance that is contained within the flowable composition adapted for implantation in body tissues can be, for example, octreotide, GHRP-1, or risperidone.

Specific Ranges, Values, and Embodiments

In one embodiment, the polyester polymer is biodegradable.

In another embodiment, the polyester is a polymer manufactured from one or more of D-lactide, L-lactide, DL-lactide, lactic acid, glycolide, glycolic acid, and e-caprolactone.

In another embodiment, the polyester is at least substantially insoluble in aqueous medium or body fluid.

In another embodiment, the polyester is thermoplastic, i.e., softens or melts upon an increase in temperature.

In another embodiment, the polyester includes one or more functional groups on at least one molecular chain end, wherein the functional group is selected from carboxylic acid, hydroxyl, alkyl, acryloyl, ester, polyethylene glycol (PEG), maleate, succinate, and citrate.

In another embodiment, the polyester includes one or more functional groups attached to the chain of the polyester molecule, wherein the functional group is selected from carboxylic acid, hydroxyl, alkyl, acryloyl, ester, polyethylene glycol (PEG), maleate, succinate, and citrate.

In another embodiment, the polyester is a homopolymer of lactide, glycolide, or caprolactone, or a copolymer of any combination of lactide, glycolide and caprolactone.

In another embodiment, the polyester is poly(DL-lactide-co-glycolide) (PLG).

In another embodiment, the polyester is PLG having a molar ratio of lactic acid to glycolic acid of about 50/50 to about 99/1.

In another embodiment, the polyester is 100% PLA.

In another embodiment, the polyester is 50/50 poly (DL-lactide-co-glycolide) having a carboxy terminal group.

In another embodiment, the polyester is 75/25 poly (DL-lactide-co-glycolide) without a carboxy terminal group.

In another embodiment, the terminal groups of the poly (DL-lactide-co-glycolide) can either be hydroxyl, carboxyl, or ester.

In another embodiment, the polyester has an average molecular weight (Mw) of about 15 kDa to about 45 kDa.

In one embodiment, the supercritical fluid includes carbon dioxide.

In another embodiment, the supercritical fluid includes at least about 99 wt. % carbon dioxide.

In another embodiment, the supercritical fluid is substantially pure carbon dioxide.

In another embodiment, the supercritical fluid is carbon dioxide that is at least about 99 wt. % pure.

In another embodiment, the supercritical fluid is carbon dioxide that includes at least about 1 wt. % of a co-solvent.

In another embodiment, the supercritical fluid is carbon dioxide that includes at least about 5 wt. % of a co-solvent.

In another embodiment, the supercritical fluid is carbon dioxide that includes at least one of Xenon (Xe), Freon-23, ethane, $N_2O$, $SF_6$, propane, ammonia, ethylene, n-$C_4H_{10}$, $(C_2H_5)_2O$, THF, methylene chloride, chloroform, $C_6H_5CF_3$, p-$C_1$-$C_6H_4CF_3$, methanol, ethanol, 1-propanol, 2-propanol, 1-hexanol, 2-methoxy ethanol, tetrahydrofuran, 1,4-dioxane, acetonitrile, propylene carbonate, N,N-dimethylacetamide, dimethyl sulfoxide, N-methylpyrrolidone, formic acid, water, carbon disulfide, acetone, propane, toluene, hexanes, and pentanes; as a co-solvent.

In one embodiment, the polyester is extracted with the supercritical fluid at about room temperature.

In another embodiment, the polyester is extracted with the supercritical fluid below about room temperature.

In another embodiment, the polyester is extracted with a solvent at an elevated temperature (i.e., above room temperature).

In another embodiment, the polyester is extracted with the supercritical fluid at a single elevated temperature.

In another embodiment, the polyester is sequentially extracted with the supercritical fluid at multiple elevated temperatures, such as extractions at a series of increasing temperatures.

In one embodiment, the elevated temperature is at least above about 50° C.

In one embodiment, the polyester is extracted with the supercritical fluid at a single elevated pressure.

In another embodiment, the polyester is sequentially extracted with the supercritical fluid at multiple elevated pressures, such as extractions at a series of increasing pressures.

In one embodiment, the elevated pressure is above about 1,000 psi.

In one embodiment, the purified biodegradable polyester has a narrower molecular weight distribution than the polyester prior to extraction with the supercritical fluid.

In one embodiment, the purified biodegradable polyester has a polydispersity index of less than about 1.7.

In one embodiment, the purified polyester includes less than about 10 wt. % of oligomers having a molecular weight of up to about 5 kDa.

In one embodiment, the purified polyester includes less than about 2 wt. % of monomers.

In one embodiment, a controlled release formulation adapted for implantation within body tissues comprises a SFE-purified PLG copolymer according to the invention, an organic solvent that has at least some solubility in water or body fluids, and a bioactive substance. The organic solvent can be NMP. The bioactive substance can be octreotide, or GHRP-1, or risperidone. The controlled release formulation is adapted to release the respective bioactive substance over a period of time at a substantially constant rate. Use of an inventive PLG copolymer in a controlled release formulation of this type can reduce the initial burst effect of the bioactive substance relative to a controlled release formulation using a biodegradable polymer that has not undergone the inventive purification method.

All cited publications, patents, and patent applications are incorporated herein by reference and form part of this invention. While in the foregoing specification this invention has been described in relation to certain preferred embodiments thereof, and many details have been set forth for purposes of illustration, it will be apparent to those skilled in the art that the invention includes additional embodiments and that certain of the details described herein may be varied considerably without departing from the basic principles of the invention. The present invention can be illustrated by the following non-limiting examples.

EXAMPLES

Example 1

Fractionation Procedure and Results

Supercritical fluid extraction (SFE) fractionation of a PLG copolymer was examined as a method for narrowing the molecular weight distribution of this polyester to obtain PLG copolymer fractions with a reduced initial burst effect in controlled release formulations such as Atrigel®. A single lot of polyester was fractionated using generic SFE processing conditions with no process development or optimization. The polyester examined in the experiment was an 85:15 lactide/glycolide PLG (Part No. 01280, Lot 2137) with a weight average molecular weight ($M_w$) of 25 kDa, using an apparatus as illustrated in FIG. 1.

A sample of 20.4 g of the PLG polyester was loaded into the extraction vessel and processed by multiple sequential extractions of pure supercritical carbon dioxide, using a $CO_2$ pressure profile to fractionate the polyester into seven sequential fractions (see Table 1, below). The first fraction that was collected resulted from supercritical extraction at a relatively low pressure, and each subsequent fraction that was collected resulted from supercritical extraction at consecutively higher pressures. Each soluble fraction was precipitated and collected in a glass U-tube down stream from a pressure reduction valve where the $CO_2$ was evaporated at atmospheric pressure. All of the polyester charged into the extraction vessel was recovered in the seven fractions, with 103% mass recovery, with most of the mass recovered in fraction numbers 5 and 6.

Figure 2:
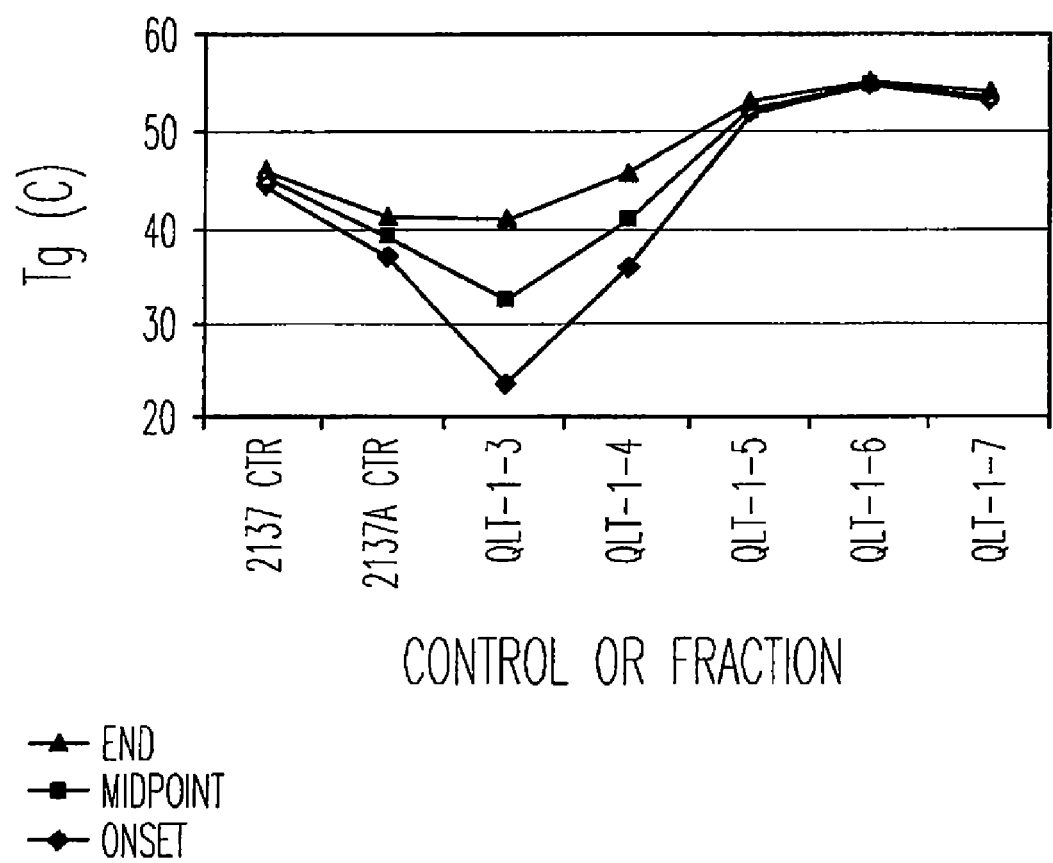
FIG. 2 depicts a graph of glass transition temperatures for Supercritical Fluid Extraction (SFE) Fractionated poly(DL-lactide-glycolide) fractions.

Table 1 shows the GPC $M_w$ of the PLG obtained from each fraction, and the nuclear magnetic resonance (NMR) derived monomer and copolymer contents, for each of the seven SFE fractions and for the original control material, and the control material after a standard solvent precipitation purification. Table 2 and FIG. 2 show the DSC glass transition temperature (Tg) onset, midpoint, and end temperatures for the control (lot 2137), five of the seven SFE fractions, and the control after standard solvent precipitation purification (lot 2137A). Table 3 shows the weight average molecular weight, polydispersity index, wt % of polymer (oligomer) having weight average molecular weights of <1 kDa, <3 kDa, <5 kDa and <10 kDa, the sum of those values, wt % of monomers, and the mole % of lactide and of glycolide.

The data show that the polyester was successfully fractionated according to molecular weight and that the fractions generally had a narrower molecular weight distribution than the control starting material. The fractions also contained less residual lactide and glycolide monomer than the original control material with levels similar to the solvent precipitation purified material. The molar ratio of lactic acid to glycolic acid in the polyester was not significantly changed by the fractionation, however, as shown in FIG. 2, the Tg of the fractions were significantly different from the controls.

Table 3 unexpectedly shows that a reduced oligomer content is not sufficient to explain the improved properties of the two purified fractions 5 and 6 with respect to the unpurified PLG. For example, fraction 5 appears to have about the same oligomer content, that is, the wt % of polymers of <3 kDa, <5 kDa, and <10 kDa, as does the unpurified polymer, although fraction 6 does have lower contents of these oligomer materials. However, both fractions 5 and 6 exhibit improved properties in terms of initial burst. This appears to be at variance with documents described in the Background section, wherein improved initial burst properties of various purified PLG copolymers are attributed to reduced oligomer content. The reasons for the improved initial burst properties of these fractions 5 and 6 are not completely understood, but may relate to their narrower molecular weight distribution (polydispersity index).

TABLE 1

Molecular Weight Results for SFE Fractionated PLGH

| | GPC Results | | % of | NMR Results | | | |
|---|---|---|---|---|---|---|---|
| Fraction | Mw (kDa) | Mw/Mn | Total Mass | Lactide % w/w | Glycolide % w/w | Mole % PLA | Mole % PGA |
| Control | 25 | 1.84 | n.a. | 2.36% | 0.10% | 83.88% | 16.12% |
| 1 | 0 | 1.23 | 1.5% | 0.00% | 0.00% | 76.48% | 23.52% |
| 2 | 1 | 1.15 | 2.5% | 0.00% | 0.00% | 71.12% | 28.88% |
| 3 | 8 | 2.28 | 7.0% | 0.71% | 0.00% | 85.57% | 14.43% |
| 4 | 12 | 2.11 | 12.0% | 1.35% | 0.03% | 85.06% | 14.94% |
| 5 | 20 | 1.65 | 39.0% | 0.61% | 0.05% | 84.31% | 15.69% |
| 6 | 35 | 1.44 | 36.0% | 0.32% | 0.00% | 83.46% | 16.54% |
| 7 | 36 | 1.43 | 5.0% | 0.54% | 0.06% | 83.19% | 16.81% |
| Precip. | 25 | 1.76 | n.a. | 0.6% | 0.0% | — | — |

TABLE 2

Glass Transition Temperatures for SFE Fractionated PLGH

| Sample ID | Onset | Midpoint | End | Range |
|---|---|---|---|---|
| 2137 Control | 44.26 | 44.98 | 45.67 | 1.41 |
| 2137A Control | 36.81 | 39.04 | 41.30 | 4.49 |
| QLT-1-3 | 23.62 | 32.35 | 41.01 | 17.39 |
| QLT-1-4 | 36.07 | 40.94 | 45.79 | 9.72 |
| QLT-1-5 | 51.99 | 52.49 | 52.99 | 1.00 |
| QLT-1-6 | 54.75 | 55.00 | 55.29 | 0.54 |
| QLT-1-7 | 53.04 | 53.61 | 54.16 | 1.12 |

See also FIG. 2 for graphical representation of these results.

TABLE 3

Compositions of SFE-fractionated PLG

| Fraction | Mw (kDa) | Mw/Mn | % Poly <1 kDa | % Poly <3 kDa | % Poly <5 kDa | % Poly <10 kDa | % of Total Wt. | Lactide % w/w | Glycolide % w/w | Mole % PLA | Mole % PGA |
|---|---|---|---|---|---|---|---|---|---|---|---|
| Ctr | 25 | 1.84 | 0.0% | 2.2% | 6.0% | 19.0% | n.a. | 2.36% | 0.10% | 83.88% | 16.12% |
| 1 | 0 | 1.23 | 96.9% | 98.8% | 98.8% | 100.0% | 1.5% | 0.00% | 0.00% | 76.48% | 23.52% |
| 2 | 1 | 1.15 | 30.0% | 99.0% | 100.0% | 100.0% | 2.5% | 0.00% | 0.00% | 71.12% | 28.88% |
| 3 | 8 | 2.28 | 4.1% | 25.2% | 43.7% | 72.2% | 7.0% | 0.71% | 0.00% | 85.57% | 14.43% |
| 4 | 12 | 2.11 | 1.6% | 10.9% | 22.8% | 52.0% | 12.0% | 1.35% | 0.03% | 85.06% | 14.94% |
| 5 | 20 | 1.65 | 0.0% | 2.1% | 6.7% | 24.4% | 39.0% | 0.61% | 0.05% | 84.31% | 15.69% |
| 6 | 35 | 1.44 | 0.0% | 0.1% | 0.7% | 4.5% | 36.0% | 0.32% | 0.00% | 83.46% | 16.54% |
| 7 | 36 | 1.43 | 0.0% | 0.0% | 0.6% | 4.2% | 5.0% | 0.54% | 0.06% | 83.19% | 16.81% |

Example 2

Method of Measuring the Molecular Weights (Mw) of Polyesters

1. Prepare the Polyester Laboratories PS-2 EasiCal narrow range polystyrene standards A and B by dissolving the pre-formed standard spatulas A and B into separate vials with 5.0 mL of THF.
2. Prepare all required controls by dissolving each raw polyester into THF to make approx. 0.5% w/v solutions of each control.

3. Prepare all polyester raw material samples by dissolving each into THF to make approx. 0.5% w/v solutions of each sample.
4. Transfer each standard, control, sample solution, and some blank THF into separate autosampler vials for analysis.
5. Condition an HPLC system to achieve a stable baseline with the following parameters:
Column—Polyester Laboratories PLgel MIXED-D, 5 micron×30 cm×7.5 mm GPC column, or equivalent
Guard Column—PLgel 5 micron guard column, or equivalent
HPLC—equipped with differential refractive index detector with controlled temperature, controlled temperature column compartment, and software capable of GPC evaluation, or equivalent
Mobile Phase—THF
Flow Rate—1.0 mL/min
Column Temperature—40° C.
Detector Temperature—40° C.
6. Create an analysis sequence to run the vials in the following order using the parameters listed below: blank, standard A and B, controls, samples (reanalyze the blank and controls after every 20 samples and at the end of the sequence)
Injection Volume—50 microliters
Run Time—15 minutes
7. Calibrate with standard A and B using third-order regression and process the controls and samples using GPC evaluation software to determine weight average and number average molecular weights (Mw and Mn, respectively) and polydispersity (Mw/Mn).

Dissolve each polystyrene standard in 5.0 mL of THF. Dissolve all controls and samples in THF to a concentration of approx. 0.5% w/v.

Transfer standards, controls, samples, and blank THF into separate autosampler vials.

Condition an HPLC system configured according to the afore-mentioned parameters to achieve a stable base line.

Create an analysis sequence to run the vials in the following order using the afore mentioned parameters: blank, standards, controls, samples (reanalyze the blank and controls after every 20 samples and at the end of the sequence).

Calibrate with the standards using third-order regression and process the controls and samples using GPC evaluation software to determine weight average and number average molecular weights (Mw and Mn, respectively) and polydispersity (Mw/Mn).

Note, the Standards A and B were prepared to be 0.1% w/v total material for each standard. Each of these standards has five peaks of different Mw which means that each of the individual peaks is 0.02% w/v (i.e. 200 ppm) in concentration.

Note, one of the controls that was run is a Mid-Range Broad-Range (MRBR) polystyrene standard made by the same company that makes the A and B standards. This particular control is at a concentration of 0.1% w/v while the other in-house made controls that we run are at 0.5% w/v.

Example 3

Figure 3:
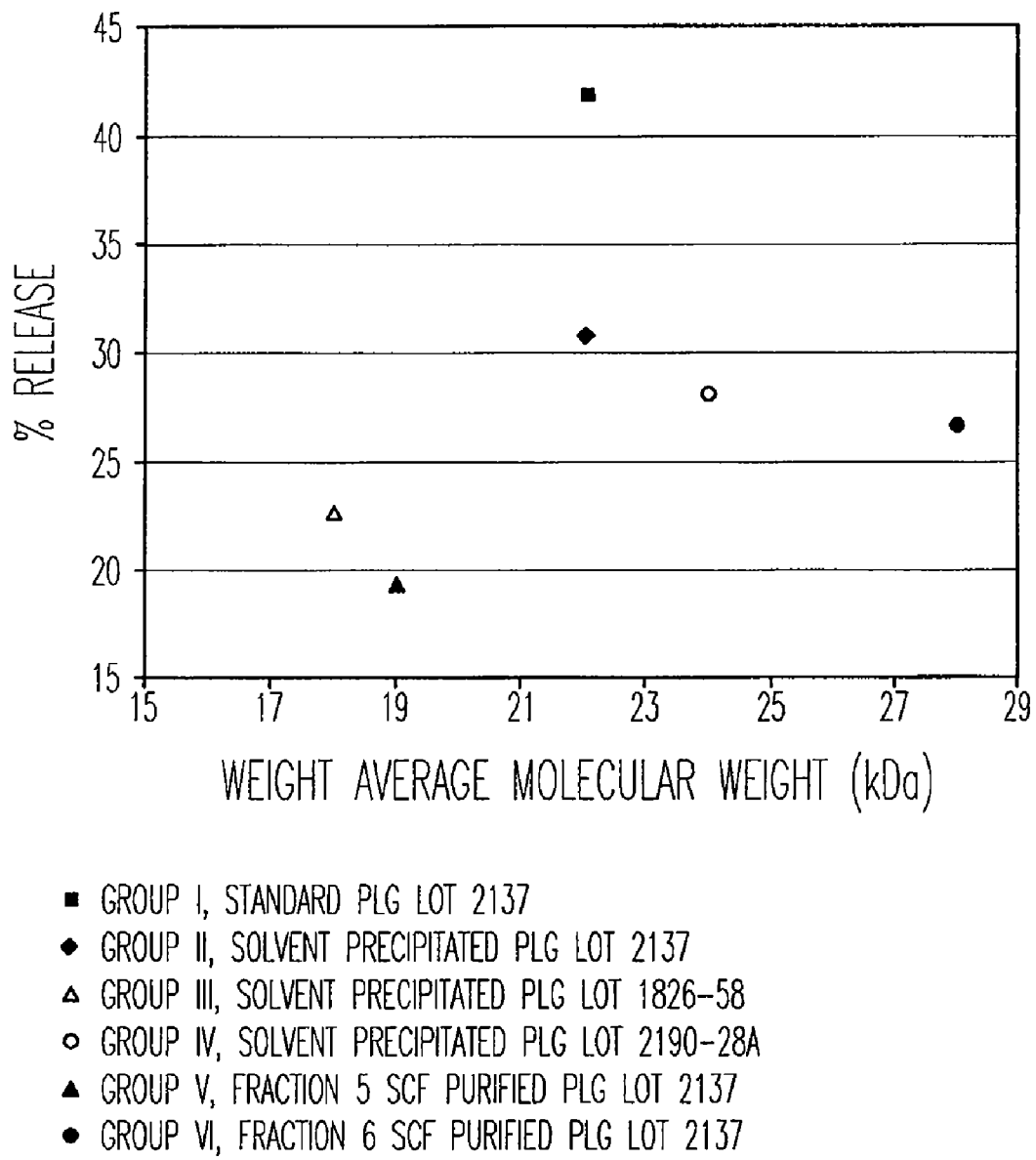
FIG. 3 depicts a graph of a 24-hour release profile of octreotide acetate in rats from a controlled release formulation comprising an unpurified PLG copolymer (PLGH), a solvent-precipitation purified PLG copolymer (PLGHp), and fractions 5 and 6 (from Table 1) of the supercritical fluid extraction (SFE) purified PLG copolymer according to the method of the invention.

Reduction in Initial Burst Effect of Purified Biodegradable PLG Flowable Controlled Release Compositions in Rats Table 4, below, and FIG. 3 show the results of a study in rats of the 24 hour release of octreotide from flowable controlled release formulations that all contain the same weight percentage of purified and unpurified 85/15 lactide/glycolide PLG samples. Each delivery system is 50% polymer and 50% N-methylpyrrolidone (NMP) and was gamma irradiated at 18-28 kGray. Just prior to injection the delivery system was mixed with the contents of a drug syringe. Each drug syringe contained the product of lyophilization of an aqueous solution of octreotide acetate and citric acid as described in patent application U.S. Ser. No. 11/667,443, filed May 9, 2007 and incorporated herein by reference. In this study, flowable compositions containing octreotide were implanted in rats, and the amount of the contained octreotide released in the first 24 hours after implantation was determined. Thus, higher percentages of initial release within this time period indicate a high initial burst effect, whereas lower percentages indicate a desirable lower initial burst effect. Group I, using standard PLG copolymer lot 2137, unpurified, was injected into five individuals, and the mean percentage release of octreotide in the first 24 hours implantation was found to be 41.9%, with a standard deviation of 8.0%. Group II, using solvent precipitation purified PLG (lot 2137 PLG was dissolved in dichloromethane and precipitated with methanol) showed a mean initial release of octreotide of 30.8% with a standard deviation of 8.6%. Groups III and IV, two additional solvent precipitation purified PLG samples, showed initial release percentages of 22.7% (SD 3.5%) and 28.2% (SD 7.7%) respectively. Group V, Fraction 5, an SFE purified PLG polyester prepared as described in Example 1, showed an initial release of 19.5% (SD 4.6%), and Group VI, Fraction 6 of the sequential SFE procedure of Example 1, showed an initial release of 26.8% (SD 5.8%).

In FIG. 3, the solid square shows the post-irradiation $M_w$ and the percentage 24 hour octreotide release from lot 2137 PLG ("PLGH"), the solid diamond shows the $M_w$ and the percentage 24 hour octreotide release from solvent-precipitation purified lot 2137 PLG, and the solid triangle and solid circle show the $M_w$s and the percentages 24 hour octreotide release from fractions 5 and 6 respectively, from Example 1 (above) of SFE purified lot 2137 PLG. The open triangle and open circle show $M_w$ and 24 hour octreotide release from two other solvent precipitation purified 85/15 PLG samples.

TABLE 4

24-Hour release profile of octreotide acetate in rats

| Group | Polymer Lot | Post-Irradiation Molecular Weight (kDa) | Sample | Cumulative Release | Mean | Standard Deviation |
|---|---|---|---|---|---|---|
| I | 2137 | 22 | S-001 | 37.6% | 41.9% | 8.0% |
| | | | S-002 | 51.9% | | |
| | | | S-003 | 48.7% | | |
| | | | S-004 | 32.7% | | |
| | | | S-005 | 38.8% | | |
| II | 2137a (solvent purified) | 22 | S-006 | 28.4% | 30.8% | 8.6% |
| | | | S-007 | 42.6% | | |
| | | | S-008 | 30.8% | | |
| | | | S-009 | 33.4% | | |
| | | | S-010 | 18.9% | | |
| III | 1826-58 (solvent purified) | 18 | S-011 | 26.7% | 22.7% | 3.5% |
| | | | S-012 | 21.8% | | |
| | | | S-013 | 22.1% | | |
| | | | S-014 | 17.7% | | |
| | | | S-015 | 25.1% | | |
| IV | 2190-28a (solvent purified) | 24 | S-016 | 41.9% | 28.2% | 7.7% |
| | | | S-017 | 23.2% | | |
| | | | S-018 | 25.4% | | |
| | | | S-019 | 25.6% | | |
| | | | S-020 | 24.9% | | |

TABLE 4-continued

24-Hour release profile of octreotide acetate in rats

| Group | Polymer Lot | Post-Irradiation Molecular Weight (kDa) | Sample | Cumulative Release | Mean | Standard Deviation |
|---|---|---|---|---|---|---|
| V | Fraction 5 (from SFE purification of lot 2137) | 19 | S-021 | 19.6% | 19.5% | 4.6% |
|  |  |  | S-022 | 23.6% |  |  |
|  |  |  | S-023 | 24.7% |  |  |
|  |  |  | S-024 | 14.8% |  |  |
|  |  |  | S-025 | 15.0% |  |  |
| VI | Fraction 6 (from SFE purification of lot 2137) | 28 | S-026 | 33.7% | 26.8% | 5.8% |
|  |  |  | S-027 | 32.0% |  |  |
|  |  |  | S-028 | 22.2% |  |  |
|  |  |  | S-029 | 25.4% |  |  |
|  |  |  | S-030 | 20.8% |  |  |

Example 4

Reduction in Initial Burst Effect of Purified Biodegradable PLG Flowable Controlled Release Compositions Incorporating GHRP-1 or Risperidone A flowable composition is prepared from an 85/15 lactide/glycolide PLG copolymer that is SFE-purified is dissolved in an equal weight of N-methylpyrrolidone and radiation-sterilized in a syringe as described in Example 3. A drug syringe containing a lyophilized sample of GHRP-1 (growth hormone releasing peptide-1), or a lyophilized sample of risperidone, respectively, is mixed with the solution of the SFE-purified PLG copolymer in N-methylpyrrolidone by reciprocating exchange of the contents of the two syringes. The controlled release formulation is then injected into the body tissue of a living mammal, wherein the GHRP-1 or the risperidone is released at a substantially constant rate over a period of time, such as over about 30 days, or about 60 days, or about 90 days. A reduced initial burst effect, i.e., a reduced amount of immediate release, within the first approximately 24 hours after implantation, relative to a controlled release formulation incorporating an unpurified PLG copolymer, is observed.

The invention claimed is:

1. A method for obtaining a purified biodegradable PLG copolymer polyester, the method comprising extracting a poly(DL-lactide-glycolide) (PLG) polyester with a supercritical fluid comprising carbon dioxide to obtain the purified biodegradable PLG copolymer polyester, wherein the purified biodegradable PLG copolymer polyester dissolves in the supercritical fluid and is recovered by evaporation of the supercritical fluid, wherein the poly(DL-lactide-glycolide) (PLG) polyester is fractionated by a series of successive extractions with the supercritical fluid, wherein each successive extraction is carried out at a higher pressure; wherein a first extraction pressure is at least about 1,000 psi and the successive extractions at higher pressures are carried out at pressures increasing up to about 12,000 psi; and wherein the extractions are carried out at a temperature of at least about 50° C., optionally increasing to about 100° C. during the successive extractions.

2. The method of claim 1, wherein the poly(DL-lactide-glycolide) has been previously purified by a step of solvent precipitation.

3. The method of claim 1, wherein the purified biodegradable polyester comprises one or more functional groups on at least one molecular chain end, or one or more functional groups attached to the chain of the polyester molecule, or both, wherein the functional group is a carboxylic acid, hydroxyl, alkyl, acryloyl, ester, polyethylene glycol (PEG), maleate, succinate, or citrate group, or any combination thereof.

4. The method of claim 1, wherein the purified PLG copolymer has a molar ratio of lactic acid to glycolic acid of about 50/50 to about 99/1.

5. The method of claim 1, wherein the polyester has an average molecular weight (Mw) of about 15 kDa to about 45 kDa.

6. The method of claim 1, wherein the carbon dioxide is at least about 99 wt. % pure.

7. The method of claim 1, wherein the carbon dioxide comprises at least about 1 wt. % of a co-solvent.

8. The method of claim 1, wherein the supercritical fluid further comprises a cosolvent comprising at least one of Xenon (Xe), Freon-23, ethane, $N_2O$, $SF_6$, propane, ammonia, ethylene, n-$C_4H_{10}$, $(C_2H_5)_2O$, THF, methylene chloride, chloroform, $C_6H_5CF_3$, p-Cl-$C_6H_4CF_3$, methanol, ethanol, 1-propanol, 2-propanol, 1-hexanol, 2-methoxyethanol, tetrahydrofuran, 1,4-dioxane, acetonitrile, propylene carbonate, N,N-dimethylaceamide, dimethyl sulfoxide, N-methylpyrrolidone, formic acid, water, carbon disulfide, acetone, toluene, hexanes, or pentanes, or any combination thereof.

9. The method of claim 1, wherein the polyester is sequentially extracted at multiple increasing temperatures with successive samples of the supercritical fluid.

10. The method of claim 9, wherein the multiple temperatures range from about 50° C. to about 100° C.

11. The method of claim 8, wherein the polyester is sequentially extracted at multiple increasing temperatures with successive samples of the supercritical fluid, wherein a content of the cosolvent varies among the successive samples.

12. The method of claim 8, wherein the polyester is sequentially extracted at multiple increasing temperatures with successive samples of the supercritical fluid, wherein a content of the cosolvent varies among the successive samples.

13. The method of claim 1, wherein the purified biodegradable polyester has a narrower molecular weight distribution than the polyester.

14. The method of claim 1 wherein the purified biodegradable polyester has a polydispersity index of less than about 1.7.

15. The method of claim 1, wherein the purified biodegradable polyester, when incorporated into a controlled release formulation, provides a reduced initial burst effect.

16. The method of claim 1, wherein the purified polyester comprises less than about 10 wt. % of oligomers having a molecular weight of up to about 5 kDa, less than about 2 wt. % of monomers, or both.

17. The method of claim 1 comprising sequentially extracting PLG having an average molecular weight ($M_w$) of about 15 kDa to about 45 kDa with a supercritical fluid comprising carbon dioxide at a temperature above about 50° C. and a pressure above about 1,000 psi, wherein the purified PLG copolymer has a narrower molecular weight distribution than the PLG, a polydispersity index of less than about 1.7, the purified PLG copolymer comprises less than about 10 wt % of oligomers having $M_w$, of up to about 5 kDa, and the purified PLG copolymer comprises less than about 2 wt % of monomers.

18. A purified biodegradable PLG copolymer prepared by the method of claim 17.

19. A purified biodegradable PLG copolymer prepared by the method of claim 1.

20. The purified biodegradable PLG copolymer of claim 18 or 19 wherein the purified PLG copolymer has a reduced polydispersity index relative to the PLG, wherein the polydispersity index of the purified PLG copolymer is less than about 1.7.

21. The purified biodegradable PLG copolymer of claim 18 or 19 wherein the purified PLG copolymer has an oligomer content of less than about 10 wt %.

22. The purified biodegradable PLG copolymer of claim 18 or 19 wherein the purified PLG copolymer has a monomer content of less than about 2 wt %.

23. A controlled release formulation comprising a flowable composition comprising the purified biodegradable PLG copolymer of claim 18 or 19, and an organic solvent having at least some solubility in body fluids, and a bioactive substance.

24. The controlled release formulation of claim 23 having a reduced initial burst of the bioactive substance when implanted in a body tissue.

25. The controlled release formulation of claim 23 wherein the bioactive substance comprises octreotide.

26. The controlled release formulation of claim 23 wherein the bioactive substance comprises GHRP-1.

27. The controlled release formulation of claim 23 wherein the bioactive substance comprises risperidone.

28. The controlled release formulation of claim 23 wherein the initial burst of the bioactive substance upon implantation within body tissues is reduced.

* * * * *

UNITED STATES PATENT AND TRADEMARK OFFICE
CERTIFICATE OF CORRECTION

PATENT NO. : 8,076,448 B2  Page 1 of 1
APPLICATION NO. : 12/421535
DATED : December 13, 2011
INVENTOR(S) : Lester Moore et al.

It is certified that error appears in the above-identified patent and that said Letters Patent is hereby corrected as shown below:

On the title page, in item (56), under "Other Publications", in column 2, line 15, delete "Nork," and insert -- York, --, therefor.

On the title page, in item (56), under "Other Publications", in column 2, line 29, delete "12/421,535," and insert -- 12/421,535, Response --, therefor.

In the Claims

In column 20, line 24, in Claim 8, delete "dimethylaceamide," and insert -- dimethylacetamide, --, therefor.

In column 20, line 61, in Claim 17, delete "$M_w$," and insert -- $M_w$ --, therefor.

Signed and Sealed this
Ninth Day of December, 2014

Michelle K. Lee
*Deputy Director of the United States Patent and Trademark Office*